(12) United States Patent
Pearlman et al.

(10) Patent No.: US 10,869,847 B2
(45) Date of Patent: *Dec. 22, 2020

(54) CERAMIDE COMPOSITION AND METHOD OF USE

(71) Applicants: Case Western Reserve University, Cleveland, OH (US); The Penn State Research Foundation, University Park, PA (US)

(72) Inventors: Eric Pearlman, Irvine, CA (US); Mark Kester, Afton, VA (US)

(73) Assignees: Case Western Reserve University, Cleveland, OH (US); The Penn State Research Foundation, University Park, PA (US)

( * ) Notice: Subject to any disclaimer, the term of this patent is extended or adjusted under 35 U.S.C. 154(b) by 169 days.

This patent is subject to a terminal disclaimer.

(21) Appl. No.: 16/046,246

(22) Filed: Jul. 26, 2018

(65) Prior Publication Data

US 2019/0029978 A1    Jan. 31, 2019

Related U.S. Application Data

(62) Division of application No. 11/773,989, filed on Jul. 6, 2007, now Pat. No. 10,045,953.

(60) Provisional application No. 60/806,655, filed on Jul. 6, 2006.

(51) Int. Cl.
*A61K 9/127* (2006.01)
*A61K 31/164* (2006.01)

(52) U.S. Cl.
CPC .................................. *A61K 31/164* (2013.01)

(58) Field of Classification Search
None
See application file for complete search history.

(56) References Cited

U.S. PATENT DOCUMENTS

| | | | |
|---|---|---|---|
| 2003/0206938 A1 | 11/2003 | Pereira et al. | |
| 2019/0029978 A1* | 1/2019 | Pearlman | A61K 31/164 |

FOREIGN PATENT DOCUMENTS

| | | |
|---|---|---|
| WO | 2001/024866 A1 | 4/2001 |
| WO | 2001/072701 | 10/2001 |
| WO | 2003/005965 A2 | 1/2003 |
| WO | 2004/064823 | 8/2004 |
| WO | 2005/014008 A2 | 2/2005 |

OTHER PUBLICATIONS

Chang JH, McCluskey PJ, Wakefield D. Toll-like receptors in ocular immunity and the immunopathogenesis of inflammatory eye disease. Br J Ophthalmol 2006;90:103-108.

Yu FS, Hazlett LD. Toll-like receptors and the eye. Invest Ophthalmol Vis Sci 2006;47:1255-1263.

Johnson AC, Heinzel FP, Diaconu E, et al. Activation of toll-like receptor (TLR)2, TLR4, and TLR9 in the mammalian cornea induces MyD88-dependent corneal inflammation. Invest Ophthalmol Vis Sci 2005;46:589-595.

Khatri S, Lass JH, Heinzel FP, et al. Regulation of endotoxin-induced keratitis by PECAM-1, MIP-2, and toll-like receptor 4. Invest Ophthalmol Vis Sci 2002;43:2278-2284.

Holden BA, Reddy MK, Sankaridurg PR, et al. Contact lens-induced peripheral ulcers with extended wear of disposable hydrogel lenses: histopathologic observations on the nature and type of corneal infiltrate. Cornea 1999;18:538-543.

Futerman AH, Hannun YA. The complex life of simple sphingolipids. EMBO Rep 2004;5:777-782.

Kester M, Kolesnick R. Sphingolipids as therapeutics. Pharmacol Res 2003;47:365-371.

Ogretmen B, Hannun YA. Biologically active sphingolipids in cancer pathogenesis and treatment. Nat Rev Cancer 2004;4:604-616.

Fuortes M, Jin W, Nathan C. Ceramide selectively inhibits early events in the response of human neutrophils to tumor necrosis factor. J Leukoc Biol 1996;59:451-460.

Nakamura T, Abe A, Balazovich KJ, et al. Ceramide regulates oxidant release in adherent human neutrophils. J Biol Chem 1994;269:18384-18389.

Suchard SJ, Mansfield PJ, Boxer LA, Shayman JA. Mitogen-activated protein kinase activation during IgG-dependent phagocytosis in human neutrophils: inhibition by ceramide. J Immunol 1997;158:4961-4967.

Wong K, Li XB, Hunchuk N. N-acetylsphingosine (C2-ceramide) inhibited neutrophil superoxide formation and calcium influx. J Biol Chem 1995;270:3056-3062.

Stover T, Kester M. Liposomal delivery enhances short-chain ceramide-induced apoptosis of breast cancer cells. J Pharmacol Exp Ther 2003;307:468-475.

Stover TC, Sharma A, Robertson GP, Kester M. Systemic delivery of liposomal short-chain ceramide limits solid tumor growth in murine models of breast adenocarcinoma. Clin Cancer Res 2005;11:3465-3474.

Kruszewski FH, Walker TL, DiPasquale LC. Evaluation of a human corneal epithelial cell line as an in vitro model for assessing ocular irritation. Fundam Appl Toxicol 1997;36:130-140.

Ueta M, Nochi T, Jang MH, et al. Intracellularly expressed TLR2s and TLR4s contribution to an immunosilent environment at the ocular mucosal epithelium. J Immunol 2004;173:3337-3347.

Adhikary G, Crish J, Lass J, Eckert RL. Regulation of involucrin expression in normal human corneal epithelial cells: a role for activator protein one. Invest Ophthalmol Vis Sci 2004;45:1080-1087.

Sun Y, Hise AG, Kalsow CM, Pearlman E. *Staphylococcus aureus*-induced corneal inflammation is dependent on Toll-like receptor 2 and myeloid differentiation factor 88. Infect Immun 2006;74:5325-5332.

(Continued)

*Primary Examiner* — Michael D Burkhart
(74) *Attorney, Agent, or Firm* — Renner, Otto, Boisselle & Sklar, LLP

(57) ABSTRACT

A method for treating and preventing diseases associated with neutrophil infiltration, particularly ocular diseases, is provided, which method comprises administering to a subject in need thereof an effective amount of ceramide or a derivative thereof. Also provided is a composition for treating diseases associated with neutrophil infiltration, the composition comprising ceramide or a derivative thereof.

15 Claims, 9 Drawing Sheets

(56) References Cited

OTHER PUBLICATIONS

Hauert AB, Martinelli S, Marone C, Niggli V. Differentiated HL-60 cells are a valid model system for the analysis of human neutrophil migration and chemotaxis. Int J Biochem Cell Biol 2002;34:838-854.

Zhang J, Xu K, Ambati B, Yu FS. Toll-like receptor 5-mediated corneal epithelial inflammatory responses to Pseudomonas aeruginosa flagellin. Invest Ophthalmol Vis Sci 2003;44:4247-4254.

Kumar A, Zhang J, Yu FS. Innate immune response of corneal epithelial cells to *Staphylococcus aureus* infection: role of peptidoglycan in stimulating proinflammatory cytokine secretion. Invest Ophthalmol Vis Sci 2004;45:3513-3522.

Bourbon NA, Sandirasegarane L, Kester M. Ceramide-induced inhibition of Akt is mediated through protein kinase Czeta: implications for growth arrest. J Biol Chem 2002;277:3286-3292.

Charles R, Sandirasegarane L, Yun J, et al. Ceramide-coated balloon catheters limit neointimal hyperplasia after stretch injury in carotid arteries. Circ Res 2000;87:282-288.

Hayashi F, Means TK, Luster AD. Toll-like receptors stimulate human neutrophil function. Blood 2003;102:2660-2669.

Lin M, Carlson E, Diaconu E, Pearlman E. CXCL1/KC and CXCL5/LIX are produced selectively by corneal fibroblasts and mediate neutrophil infiltration to the corneal stroma in LPS keratitis. J Leukoc Biol 2006.

Wang G, Silva J, Krishnamurthy K, Tran E, Condie BG, Bieberich E. Direct binding to ceramide activates protein kinase Czeta before the formation of a pro-apoptotic complex with PAR-4 in differentiating stem cells. J Biol Chem 2005;280:26415-26424.

Sweeney EA, Sakakura C, Shirahama T, et al. Sphingosine and its methylated derivative N,N-dimethylsphingosine (DMS) induce apoptosis in a variety of human cancer cell lines. Int J Cancer 1996;66:358-366.

Kim TI, Pak JH, Tchah H, Lee SA, Kook MS. Ceramide-induced apoptosis in rabbit corneal fibroblasts. Cornea 2005;24:72-79.

Ginis I, Jaiswal R, Klimanis D, Liu J, Greenspon J, Hallenbeck JM. TNF-alpha-induced tolerance to ischemic injury involves differential control of NF-kappaB transactivation: the role of NF-kappaB association with p300 adaptor. J Cereb Blood Flow Metab 2002;22:142-152.

Furuya K, Ginis I, Takeda H, Chen Y, Hallenbeck JM. Cell permeable exogenous ceramide reduces infarct size in spontaneously hypertensive rats supporting in vitro studies that have implicated ceramide in induction of tolerance to ischemia. J Cereb Blood Flow Metab 2001;21:226-232.

Yan F, Polk DB. Kinase suppressor of ras is necessary for tumor necrosis factor alpha activation of extracellular signal-regulated kinase/mitogen-activated protein kinase in intestinal epithelial cells. Cancer Res 2001;61:963-969.

Yan F, John SK, Wilson G, Jones DS, Washington MK, Polk DB. Kinase suppressor of Ras-1 protects intestinal epithelium from cytokine-mediated apoptosis during inflammation. J Clin Invest 2004;114:1272-1280.

Walton KA, Gugiu BG, Thomas M, et al. A role for neutral sphingomyelinase activation in the inhibition of LPS action by phospholipid oxidation products. J Lipid Res 2006;47:1967-1974.

Powell DJ, Hajduch E, Kular G, Hundal HS. Ceramide disables 3-phosphoinositide binding to the pleckstrin homology domain of protein kinase B (PKB)/Akt by a PKCzeta-dependent mechanism. Mol Cell Biol 2003;23:7794-7808.

Fox TE, Houck KL, O'Neill S M, et al. Ceramide recruits and activates PKCzeta within structured membrane microdomains. J Biol Chem 2007.

Siess W, Essler M, Brandi R. Lysophosphatidic acid and sphingosine 1-phosphate: two lipid villains provoking cardiovascular diseases? IUBMB life 2000;49:167-171.

Fox TE, Han X, Kelly S, et al. Diabetes alters sphingolipid metabolism in the retina: a potential mechanism of cell death in diabetic retinopathy. Diabetes 2006;55:3573-3580.

Kim TI, Lee SY, Pak JH, Tchah H, Kook MS. Mitomycin C, ceramide, and 5-fluorouracil inhibit corneal haze and apoptosis after PRK. Cornea 2006;25:55-60.

Fox TE, Finnegan CM, Blumenthal R, Kester M. The clinical potential of sphingolipid-based therapeutics. Cell Mol Life Sci 2006;63:1017-1023.

Yun JK, Kester M. Regulatory role of sphingomyelin metabolites in hypoxia-induced vascular smooth muscle cell proliferation. Arch Biochem Biophys 2002;408:78-86.

Fortin CF, Lesur O, Fulop T, Jr. Effects of TREM-1 activation in human neutrophils: activation of signaling pathways, recruitment into lipid rafts and association with TLR4. Int Immunol 2006.

Asano-Kato, N. et al; "Treatment of Atopic Blepharitis by Controlling Eyelid Skin Water Retention Ability With Ceramide Gel Application"; The British Journal of Ophthalmology, Mar. 2003, vol. 87, No. 3, pp. 362-363.

Stover et al; "Liposomal Delivery Enhances Short-Chain Ceramide-Induced Apoptosis of Breast Cancer Cells"; Journal of Pharmacology and Experimental Therapeutics, American Society for Pharmacology and Experimental Therapeutic, vol. 307, No. 2, Nov. 2003, pp. 468-475.

International Search Report and the Written Opinion of the International Searching Authority for corresponding International Application No. PCT/US2007/072905 dated Nov. 13, 2007.

\* cited by examiner

FIG. 8A
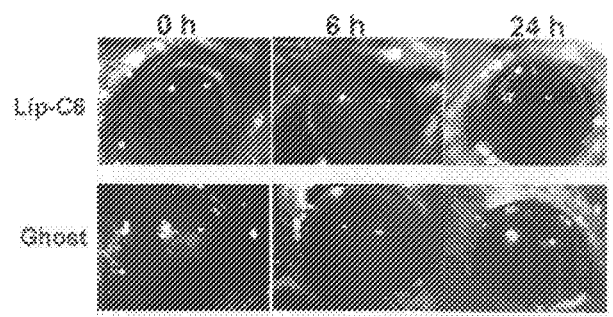
FIG. 8B
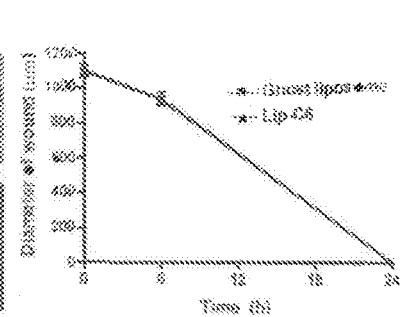
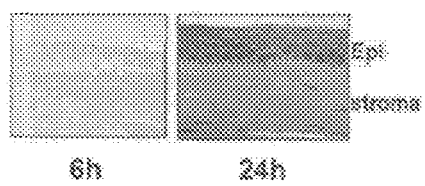
FIG. 8C
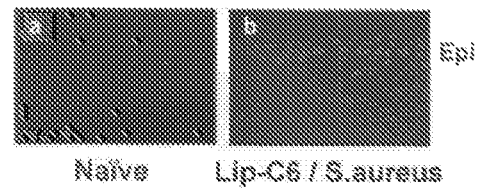
FIG. 8D

CERAMIDE COMPOSITION AND METHOD OF USE

This application is a divisional application of U.S. application Ser. No. 11/773,989 filed Jul. 6, 2007 which claims the benefit of U.S. Provisional Application No. 60/806,655 filed Jul. 6, 2006, the contents of which are hereby incorporated by reference in their entireties.

The work described herein was funded by NIH grants ROEY14362 and P30EY11373, and a Sponsored Research Agreement with Bausch and Lomb, Inc., with additional support from EY015800, The Research to Prevent Blindness Foundation and the Ohio Lions Eye Research Foundation.

BACKGROUND

Corneal infiltration and microbial keratitis are caused by viruses, bacteria, fungi and parasites, and are leading causes of visual impairment and blindness worldwide. In addition, microbial products such as lipopolysaccharide (LPS), bacterial cell walls, flagellin or microbial nucleic acid can induce corneal inflammation via Toll-like receptors (TLR) on corneal epithelial cells. TLR/MyD88-mediated CXC chemokine production and subsequent neutrophil infiltration to the corneal stroma and activation are critical steps in the inflammatory response.

SUMMARY

The present invention, in one aspect, is directed to a method for treating and/or preventing diseases associated with neutrophil infiltration, which method comprises administering an effective amount of ceramide or ceramide derivative. In one embodiment, the method comprises treating ocular disease such as keratitis, endophthalmitis, uveitis, conjunctivitis, blepharitis, contact lens-induced peripheral ulcer, corneal dystrophy, retinitis pigmentosa, diabetic retinopathy, macular degeneration, ocular toxoplasmosis and diseases resulting from complications from refractive or laser surgery.

In one aspect of the invention, there is provided a composition for treating and/or preventing diseases associated with neutrophil infiltration, the composition comprising ceramide or ceramide derivative. In one embodiment, the ceramide or ceramide derivative comprises $C_6$-ceramide. The ceramide or ceramide derivative may be delivered via a particulate carrier, particularly, a liposome.

The administration route for treating and/or preventing diseases associated with neutrophil infiltration may be at least one of intravenous, intraperitoneal, intrathecal, intralymphatic, intramuscular, intralesional, parenteral, epidural, subcutaneous, pleural, topical, oral, nasal, anal, ocular and otic. For ocular diseases, the administration route may be one of topical, systemic, intravitreal and subconjunctival.

The ceramide or ceramide derivative inhibits mitogen-activated protein (MAP) kinases signaling, particularly JNK and p38 signaling, which suppresses neutrophil recruitment to the cell. The ceramide or ceramide derivative down regulates chemotatic mediators (cytokines) that recruit neutrophils to the site of tissue injury via Toll-like and cytokine receptors.

BRIEF DESCRIPTION OF THE FIGURES

FIG. 1A: Human corneal epithelial cells (HCE-T) were pre-incubated 40 min. with Lip-C6, Lip-S1P, or control (ghost) liposomes, washed and stimulated with inactivated S. aureus, which activates TLR2 (Ref. 8). After 6 hours, supernatants were collected and CXCL1/GRO-α, CXCL5/ENA-78 and CXCL8/IL-8 were measured by ELISA. FIG. 1B: Primary human corneal epithelial cells were isolated from donor corneas, and stimulated with the synthetic TLR2 agonist Pam$_3$Cys in the presence of Lip-C6 or control, ghost liposomes. Lip-C6 inhibits chemokine production. Values are mean+/−SD for triplicate wells, and are representative of three independent experiments. (m=medium alone.)

FIGS. 2A, 2B and 2C: Human corneal epithelial cells (HCE-T) were pre-incubated 40 min with Lip-C6 or control (ghost) liposomes, washed and stimulated with S. aureus. After 3 hrs, 6 hrs, or 12 hrs, supernatants were collected and CXCL1/GRO-α (FIG. 2A), CXCL5/ENA-78 (FIG. 2B) and CXCL8/IL-8 (FIG. 2C) were measured by ELISA. FIG. 2D: Primary human corneal epithelial cells were isolated from donor corneas, pre-incubated 40 min with Lip-C6 or control liposomes, and stimulated with S. aureus. Supernatants were collected after 3 hrs, 6 hrs or 12 hrs, and cytokines were measured.

FIG. 4A: Human corneal epithelial cells were incubated with DNase I, (positive control, panel a), or with Lip-C6 (panel c), and apoptosis was detected by TUNEL assay. Panels b and d are corresponding DAPI stained nuclei. FIG. 4B: Two hundred cells were counted, and the percent TUNEL positive cells is shown. Lip C6 did not induce apoptosis in these cells.

FIGS. 8A, 8B, 8C and 8D show the effect of Lip-C6 on corneal epithelial wound healing. A 1 mm diameter corneal epithelial abrasion was generated, and corneas were treated with topical Lip-C6 or ghost liposomes 40 min prior to, and 1 and 6 h after exposure to S. aureus. A 2.5% fluorescein solution was added after 0 hr, 6 hrs or 24 hrs to detect the epithelial wound, and the diameter was calculated by image analysis. FIG. 8A: Representative images from five mice per group. FIG. 8B: Diameter of wound treated with LipC6 or ghost liposomes (mean of five corneas). There is no inhibitory effect of Lip-C6 on the rate of wound healing. FIG. 8C: Representative hematoxylin and eosin stained corneal sections 6 hrs and 24 hrs after epithelial abrasion and exposure to Lip-C6. At 6 hrs, the loss of epithelium was noted and after 24 hrs, regeneration was noted. No differences in epithelial regeneration were noted among groups treated with Lip-C6 or controls (data not shown). FIG. 8D: Corneal sections were stained with TUNEL reagents (green) to determine the effect on apoptosis, and nuclei were stained with DAPI (blue). Shown are representative sections of naïve corneas (panel a) or corneal sections after treatment with Lip-C6 and S. aureus (panel b). TUNEL positive cells were detected in the stroma and not the epithelium of S. aureus treated mice. These data are representative of three independent experiments.

FIG. 9A: The human neutrophil cell line (HL-60) was incubated with Lip-C6 or control (ghost gh) liposomes 30 min prior to stimulation with S. aureus or LPS. After 6 hrs, CXCL8/IL-8 in cell free supernatants was measured by ELISA. Results are mean+/−SD of three replicate wells, and data are representative of three independent experiments. Lip-C6 inhibited CXC chemokine production by TLR2 and TLR4 stimulated human neutrophils compared with ghost liposomes. FIGS. 9B and 9C: Murine peritoneal neutrophils (98% pure) were incubated overnight with S. aureus (FIG. 9B) or LPS (FIG. 9C) in the presence of Lip-C6 or ghost liposomes, and CXCL1/KC, CXCL2/MIP-2 were measured by ELISA. Results are mean+/−SD of three replicate wells per sample, and data are representative of three independent experiments.

DETAILED DESCRIPTION

Figure 1A:
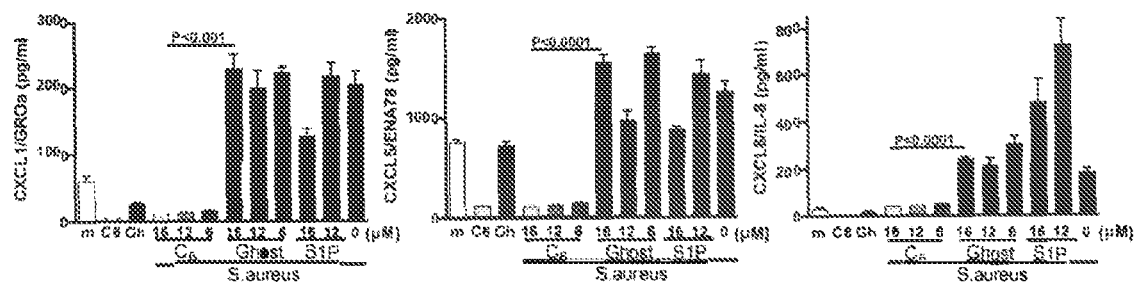
FIGS. 1A and 1B are bar graphs showing the dose dependent effect of Lip-C6 on CXC chemokine human corneal epithelial cells.

The present invention, in one aspect, is directed to a method for treating and/or preventing diseases associated with neutrophil infiltration in a cell, which method comprises administering to the cell an effective amount of ceramide or ceramide derivative. In one embodiment, the disease is ocular disease, such as an anterior eye disease including keratitis, endophthalmitis, uveitis, conjunctivitis, blepharitis, contact lens-induced peripheral ulcer and corneal dystrophy. The ocular disease may also be a disease of the posterior eye, including retinitis pigmentosa, diabetic retinopathy, macular degeneration and ocular toxoplasmosis. In one embodiment, the ocular disease is a complication resulting from refractive or laser surgery.

The administration route for administering the ceramide or ceramide derivative to the cell may be at least one of intravenous, intraperitoneal, intrathecal, intralymphatic, intramuscular, intralesional, parenteral, epidural, subcutaneous, pleural, topical, oral, nasal, anal, ocular and otic. For ocular diseases, the administration route may be one of topical, systemic, intravitreal and subconjunctival.

In one aspect of the invention, there is provided a composition for treating and/or preventing tissue injury or diseases associated with neutrophil infiltration in a cell, the composition comprising an effective amount of ceramide or ceramide derivative. The composition inhibits mitogen-activated protein (MAP) kinases signaling. The ceramide or ceramide derivative downregulates chemotatic mediators (cytokines) that recruit neutrophils to the site of tissue injury via Toll-like and cytokine receptors.

Microbial keratitis caused by bacterial infection or bacterial products is a leading cause of visual impairment, and activates the host innate immune response through pathogen recognition molecules, especially Toll-like receptors (TLR). Activation of (TLR)2, TLR4 and TLR9 on abraded corneal epithelium by bacterial lipoproteins (TLR2), lipopolysaccharide (LPS, TLR4), or bacterial DNA (TLR9) induces MyD88-dependent CXC chemokine production and subsequent neutrophil infiltration to the corneal stroma and development of corneal haze. In sterile corneal infiltrates such as contact lens associated peripheral ulcer, biopsy studies showed that neutrophils are the predominant cells present in the corneal stroma.

Sphingolipid metabolites are a class of lipids that serve both a structural role in membranes and induce intracellular signaling. Ceram ides generally include a sphingoid base linked to a fatty acid via an amide bond. The term "ceramide" as used herein refers to any N-acylsphingosine including sphingolipids in which the sphingosine is acylate with a fatty acid acyl CoA derivative to form an N-acylsphingosine. Ceram ides and ceramide derivatives include, but are not limited to, derivatives of the SN-1 position including 1-chloro and 1-benzoyl ceramides, which would not be subject to phosphorylation at this position, as well as derivatives at the SN-2 position (amide linkage), such as a methylcarbamate group or a 2-0-ethyl substituent, which would not be subject to degradation by ceramidases. In addition, cell-permeable forms of these ceramides analogs can be utilized. Examples of these cell-permeable ceramides and/or derivatives contain 2-10 carbons and have short chain fatty acids at the SN-2 position ($C_6$ ceramide). An example of $C_6$-ceramide is N-Hexanoyl-D-erythro-Sphingosine.

Ceramides may be isolated from natural sources or chemically synthesized. Ceramide mediates cell differentiation, cell cycle arrest, and apoptosis. Intracellular ceramide accumulation can lead to inhibition of Akt pro-survival pathways and stimulation of caspase activity, resulting in DNA fragmentation and cell death.

It has been previously demonstrated that $C_6$ ceramide in liposome formulation (Lip-C6) induces apoptosis of breast cancer cells and limits tumor growth. Despite the documented role of ceramide in promoting apoptosis in several cell types, this does not appear to be the mechanism of action in microbial keratitis. The mechanism involves inhibition of p38 and JNK phosphorylation, and resultant CXC chemokine production, rather than promotion of epithelial cell apoptosis. This conclusion is supported by our findings that: 1) chemokine production by human corneal epithelial cells in vitro is reduced in the absence of significant apoptosis; 2)

activation of pro-inflammatory and pro-apoptotic signaling cascades (JNK, p38) are inhibited in HCE cells by Lip-C6; 3) chemokine production by murine corneal epithelium in vivo is inhibited; 4) there is no detectable apoptosis in corneal epithelium induced by C6 in vitro or in vivo; and 5) neutrophil infiltration and development of corneal haze is inhibited in Lip-C6 treated corneas after TLR stimulation.

Ceramide in liposome formulation limits keratitis by reducing activation and production of CXC chemokines by corneal epithelial cells, and thereby limit recruitment of neutrophils to the corneal stroma. This reduction in CXC secretion may be due to Lip-C6 inhibiting pro-inflammatory cascades that involve p38 and JNK. In addition to corneal epithelial cells, neutrophil activation is also inhibited by ceramide, which represents a second target of anti-inflammatory activity.

This novel action of ceramide may also explain its role in preconditioning. For example, TNF-α generated ceramide induces tolerance to ischemia in astrocytes and intravenous or intracisternal delivery of cell permeable ceramide analogues reduce focal cerebral ischemia in SHR rats. The neutophil inhibitory actions of ceramide, may be due to ceramide-activated KSR (kinase suppressor of ras), which minimizes the pro-inflammatory and apoptotic effects of TNF in an irritable bowel disease model. Alternatively, as Akt signaling has been liked to TLR-inflammatory signaling, ceramide may exert therapeutic actions through the inhibition of Akt. Ceramide selectively interacts with protein kinase C zeta, which inactivates AKT via phosphorylation of Ser 34. In addition, ceramide can inhibit LPS/TLR4-induced IL-8 synthesis in endothelial cells. As shown in atherosclerotic and diabetic models, and confirmed in the present study using sphingosine-1-phosphate (51P, FIG. 1), it is often the phosphorylated or glycosylated ceramide metabolites, and not ceramide itself, that mediates the pro-inflammatory actions of sphinglolipids.

Topical application of C6-enriched 80 nm size nanoliposomes is an effective therapeutic approach to corneal inflammation induced by bacteria and bacterial products that activate TLRs. Furthermore, Lip-C6 functions by inhibiting CXC chemokine production by corneal epithelial cells, and thereby blocking neutrophil recruitment to the corneal stroma without inhibiting epithelial cell proliferation and wound healing. Taken together with the absence of apoptotic side effects, this provides a therapeutic application for ameliorating the clinical manifestations associated with microbial keratitis.

In certain aspects, the application provides compositions comprising a ceramide or ceramide derivative and an excipient. Such compositions may be designed for delivery systemically or locally, and may be formulated for administration in any convenient way for use in human or veterinary medicine. In certain embodiments, the ceramide or ceramide derivative composition is formulated for local delivery to a particular epithelium, optionally a mucosal epithelium. For example, a composition may be formulated for delivery to the mouth, the eye, the skin, the vagina, the rectum, the intestines and the nose or other airways. In certain embodiments, the application provides methods for making a medicament comprising a ceramide or ceramide derivative and an excipient for the administration by one of the above-described modes.

Thus, another aspect of the present invention provides compositions, optionally pharmaceutically acceptable compositions, comprising an amount, optionally a therapeutically effective amount, of ceramide, formulated together with one or more excipients, including additives and/or diluents. As described in detail below, the compositions may be specially formulated for administration in solid or liquid form, including those adapted for the following: (1) systemic or local oral administration, for example, drenches (aqueous or non-aqueous solutions or suspensions), tablets, boluses, powders, granules, pastes, or films; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. In certain embodiments the subject ceramide compounds may be incorporated into liposomal vesicles.

The phrase "therapeutically-effective amount" as used herein means that amount of a compound, material, or composition comprising a compound of the present invention that is effective for producing some desired therapeutic effect by blocking neutrophil infiltration to the site of injury.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "excipient" as used herein means a material, composition or vehicle, such as a liquid or solid filler, diluent, excipient, solvent or encapsulating material, optionally pharmaceutically-acceptable, involved in administering the subject ceramide. Each excipient should be compatible with the other ingredients of the formulation and not injurious to the subject. Some examples of materials which can serve as pharmaceutically-acceptable excipients include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The ceramide may be delivered via a particulate carrier such as a liposome. Examples of formulations of liposomes and other particulate carriers, particularly where ceramide is included as an apoptosis-inducing agent, are described in examples herein and in U.S. Patent Application Publication No. 2005/0025820. Further examples are described in Stover T et al., J Pharmacol Exp Ther., 2003, 307:468-475; and Stover T C, et al., Clin Cancer Res., 2005, 11:3465-3474. Liposomes used in methods according to the present invention typically have particle sizes in the range of about 1 nanometer to about 1 micron, inclusive, in diameter. Nano-sized liposomes having particle sizes in the range of about 1-100 nanometers, inclusive, in diameter are preferred. In embodiments in which a liposome nanocarrier is used, the liposome has a lipid-containing wall defining an internal volume.

Further particulate carriers include other nanocarriers suitable for delivering the ceramide include but are not limited to nanospheres, nanodendrimers, nanocolloids, nanodots, nanocolumns, and combinations of these. Further description of liposomes and methods relating to their preparation and use may be found in Liposomes: A Practical Approach (The Practical Approach Series, 264), V. P. Torchilin and V. Weissig (Eds.), Oxford University Press; 2nd ed., 2003. Further description of nanocarriers may be found in S. M. Moghimi et al., Nanomedicine: current status and future prospects, FASEB J. 2005, 19, 311-30.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like: (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with an excipient material to produce a single dosage form will vary depending upon the host being treated, the particular mode of administration. The amount of active ingredient that can be combined with an excipient to produce a single dosage form will generally be that amount of the compound that produces a therapeutic effect.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles and/or as tooth pastes or mouth washes and the like, each containing a predetermined amount of a compound of the present invention as an active ingredient. A compound of the present invention may also be administered as a bolus, electuary or paste.

In solid dosage forms of the invention for oral administration, the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the ceramide.

Dosage forms for the topical or transdermal (systemic) or dermal (local) administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required. In one embodiment, the ceramide or ceramide derivative is administered at a dosage of about 1 nanogram to about 100 micrograms per day. In another embodiment, the ceramide or ceramide derivative is administered at a dosage of about 100 nanograms to about 1 microgram per day.

Ophthalmic formulations, eye drops, creams, ointments, powders, solutions and the like, are also contemplated as being within the scope of this invention.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution that turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

In yet another embodiment, the ceramide can be administered as part of a combinatorial therapy with other agents. For example, the combinatorial therapy can include a ceramide with at least one antibacterial, antiviral or antifungal agent. In one embodiment, the combinational therapy includes a ceramide and at least one opthalmic antibiotic or opthalmic antiviral. Opthalmic antibiotics include, e.g., Chloromycetin opthalmic (chloramphenical); Cortisporin (neomycin and polymyxin 13 sulfates and hydrocortisone acetate cream); Ilotycin (erythromycin opthalmic ointment); NeoDecadron (neomycin sulfate-dexamethasone sodium phosphate); Polytrim (trimethoprim and polythyxin β sulfate opthalmic solution); Terra-Cortril (oxytetracycline HCl and hydrocortisone acetate); Terramycin (oxytetracycline); and TobraDex (tobramycin and dexamethasone opthalmic suspension and ointment). Opthalmic antivirals include, e.g., Vira-A opthalmic ointment, (vidarabine). Opthalmic quinalones include, e.g., Chibroxin (norfloxacin opthalmic solution); Ciloxan opthalmic solution, (Ciprofloxacin HCl); Ciloxan opthalmic ointment, (Ciprofloxacin HCl); and Ocuflox opthalmic solution (ofloxacin). Opthalmic sulfonamides include, e.g., Blephamide opthalmic ointment (sulfacetamide sodium and prednisolone acetate); and Blephamide opthalmic suspension (sulfacetamide sodium and prednisolone acetate). A combinatorial therapy may include a $C_6$-ceramide and a chemotherapeutic agent, such as cytosine, arabinoside, 5-fluorouracil, hydroxyurea, and methotrexate.

Toxicity and therapeutic efficacy of such compounds can be determined by standard pharmaceutical procedures in cell cultures or experimental animals, e.g., for determining The Ld50 (The Dose Lethal To 50% Of The Population) And The Ed50 (the dose therapeutically effective in 50% of the population). The dose ratio between toxic and therapeutic effects is the therapeutic index and it can be expressed as the ratio LD50/ED50. Compounds that exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Embodiments of inventive compositions and methods are illustrated in the following examples. These examples are provided for illustrative purposes and are not considered limitations on the scope of inventive compositions and methods.

EXAMPLES

Example 1

Preparation of Liposomal Ceramide

In general, delivery of ceramide via liposome is effective and characterized by minimal metabolic degradation, optimal subcellular localization and lower effective concentration compared to organic solvent-based, for example DMSO, delivery. (Stover T and Kester M., J Pharmacol Exp Ther., 2003, 307:468-475; and Stover T C, et al., Clin Cancer Res., 2005, 11:3465-3474).

Liposomes were prepared as described previously (see for example, Stover et al, 2003; and Stover et al., 2005) containing 30 molar % $C_6$-ceramide, 1,2-disteoroyl-sn-glycero-3-phosphocholine, 1,2-dioleoyl-sn-glycero-3-phosphoethanolamine, 1,2-distearoyl-sn-glycero-3-phosphoethanolamine-N-[methoxy PEG(2000)], PEG(750)-$C_6$-ceramide. Control liposomes were made up without ceramide, but contained the same amount of total lipids. Briefly, lipids were solubilized in chloroform, dried under a stream of nitrogen and hydrated with a phosphate-buffered saline solution at 55° C. The resulting solution was sonicated, and underwent extrusion through 100 nm polycarbonate membranes using the Avanti Mini Extruder (Avanti Polar Lipids). Liposomal-C6 vesicles had an average homogenous size distribution of 80±15 nm as measured by dynamic light scattering. Liposome C6 and control, ghost liposomes were maintained at 4° C.

Example 2

Human Corneal Epithelial (HCE) Cells

The SV-40 transfected HCE-T corneal epithelial cell line was obtained from ATCC, and maintained in keratinocyte medium as described in References 5 and 6. Primary corneal epithelial cells were obtained from corneas from the Cleveland Eye Bank, and corneal epithelial cells were released after treating with Dispase as described in Reference 7. Cells were routinely used at passages 2-5.

Example 3

Chemokine Immunoassays

HCE cells were plated into 48 well plates at $1\times10^5$/well, and incubated at times as indicated in Example 12 below. Human CXCL1, CXCL5 and CXCL8/IL-8 production was measured by ELISA according to the manufacturer's directions (R&D Systems, Minneapolis, Minn.).

Example 4

Intracellular Localization of Lip-C6

Human corneal epithelia cells were plated onto glass coverslips in a Petri dish with Keratinocyte-Serum Free Medium (KSFM). Cells were washed and incubated for 30 minutes at 4° C. with 12 µM NBD-Lip C6 (as in Refs. 3 and 4), and either 5 µM Bodipy™ labeled ceramide (Molecular Probes, Eugene, Oreg. USA) in HBSS according to manufacturer's directions, or with 40 nM MitoTracker Red (Molecular Probes). Samples were washed and examined incubate in fresh KSFM at 37° C. for a further 30 minutes. Cells were examined live using a Leica inverted scope. DMI6000B. Photomicrographs were taken using 63× objective with a 1.6 changer, giving a final magnification of ×1008.

Example 5

Apoptosis Assays

Corneal epithelial cells of five µm frozen corneal sections were incubated with terminal deoxynucleotidyl transferase-mediated dUTP nick end labeling (TUNEL) reagents according to manufacturer's directions (Roche, Penzberg, Germany). TUNEL positive cells were detected and quantified by fluorescence microscopy.

Example 6

SDS-PAGE and Western Blot Analysis

For immunoblot analysis, equivalent amounts of protein were electrophoresed on denaturing and reducing 8% polyacrylamide gels and transferred to nitrocellulose membrane. The membrane was blocked by 5% nonfat dry milk and then incubated with antibody specific for phospho-JNK (#9251), phospho-p38MAPK (#9216) JNK (#9252), and p38 MAPK (#9212 (Cell Signaling Technology, Beverly, Mass.). Antibody specific for actin was purchased from Sigma-Aldrich and used for immunoblot detection at a dilution of 1:3000. Peroxidase conjugated goat anti-mouse IgG (SC-2005) and goat anti-rabbit IgG (SC-2004) were obtained from Santa Cruz Biotechnology and used at dilution of 1:5000. Secondary antibody binding was visualized using a commercial chemiluminescence detection kit (Amersham Bioscience). The intensity of the bands in X-ray film were quantified by "ImageJ" software, and calculated as ratio of P-p38 and P-JNK over total p38 and JNK. Error bars are mean of two separated experiments with similar results.

Example 7

Mouse Model of Keratitis

C57BL/6 mice (6-8 weeks old) from The Jackson Laboratory (Bar Harbor, Me.) were anesthetized by intraperitoneal injection of 0.4 ml 2,2,2-tribromoethanol (TBE), and a 1 mm diameter area of the central corneal epithelium was defined using a trephine, and epithelium was removed using an Algerbrush™ (Richmond Products, Albuquerque, N. Mex.). Corneas were then treated with ultrapure lipopolysaccharide (LPS) from Invivogen, San Diego, Calif.) as described in References 1 and 2, or with *S. aureus* strain 8325 that had been killed by exposure to ultraviolet radiation (Ref. 8). Mice were maintained in specific pathogen-free conditions in microisolater cages, and were treated in accordance with the guidelines provided in the ARVO statement for the Use of Animals in Ophthalmic and Vision Research.

Example 8

Immunohistochemistry

Eyes were snap frozen in liquid nitrogen, and 5 µm sections were incubated 2 hrs with anti-neutrophil antibody NIMP-R14 diluted 1:100 in 1% fetal calf serum/TBS (1% FCS/TBS) as described in Reference 2. After washing, corneal sections were incubated with FITC-conjugated rabbit anti-rat antibody (Vector Laboratories, Burlingame, Calif.) diluted 1:200 in 1% FCS/TBS. Slides were mounted in Vectashield containing DAPI (Vector), and neutrophils in each section was quantified by fluorescence microscopy.

Example 9

In Vivo Confocal Microscopy Analysis of Corneal Thickness and Haze

In vivo analysis of cellular infiltration was accomplished using a Nidek Confoscan™ as described in Reference 1. Briefly, mice were anesthetized and immobilized, and the cornea was examined using a 40× objective with a transparent gel (Genteal, Novartis Ophthalmics, Duluth, Ga.) as a medium. A series of images of the entire cornea was captured using NAVIS™ software, and stromal thickness (area between basal epithelium and corneal endothelium) was measured directly using the Navis™ software. To measure stromal haze, the light intensity of each 1-2 µm image of the corneal stroma was exported into Prism (Graph Pad Software, San Diego, Calif.), and the total area under the curve was then calculated as described in References 1 and 8.

Example 10

Wound Healing Assays

For the fluorescein dye exclusion assay, 0.25% fluorescein solution (Bausch and Lomb, Inc, Rochester, N.Y.) was applied as a single drop to the ocular surface, and fluorescein was detected by fluorescence microscopy, and the area of the lesion was calculated using ImagePro™ software. Eyes were then fixed in 10% formaldehyde, embedded in paraffin, and 5 µm sections were stained with hematoxylin and eosin.

Example 11

In Vitro Neutrophil Activation

The human HL-60 cell line was maintained in RPMI with 10% FBS, and incubated five days in 1.2% DMSO to generate the neutrophil phenotype (Ref. 9). Cells were placed into 96 well plates at $1 \times 10^5$ per well, and incubated 6 hrs with S. aureus or LPS. CXCL8/IL-8 production was measured by ELISA (R&D Systems, Minneapolis, Minn.).

Murine peritoneal neutrophils were obtained as described in Reference 8. Briefly, mice were injected with 1 ml of 9% casein 16 hrs and 3 hrs prior to peritoneal lavage, and cells were layered onto a sterile 90% Percoll gradient (Pharmacia, Biotech, Piscataway, N.J.). The neutrophil population (>95%) was recovered from the second layer on the gradient as determined by cytology. Neutrophils were incubated in DMEM for 2 hrs at 37° C. with 50 ng/ml GM-CSF, and stimulated for 15 hrs with S. aureus or LPS. Viability was >95% as determined by Trypan blue exclusion Cytokines in the culture supernatants were measured by ELISA (R&D Systems).

Example 12

Lip-C6 Inhibition of TLR Activation of HCE Cells

Figure 1B:
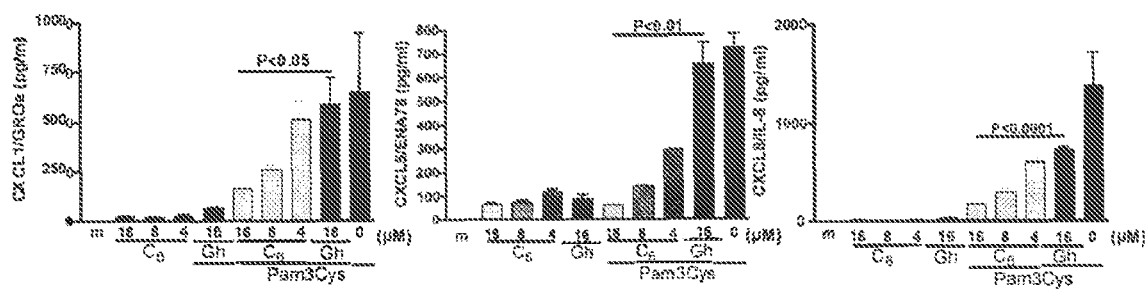
Figure 2A:
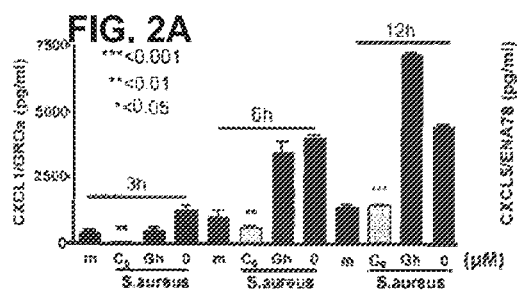
FIGS. 2A, 2B, 2C and 2D are bar graphs showing the time-dependent effect of Lip-C6 on CXC chemokine human corneal epithelial cells.
Figure 2B:
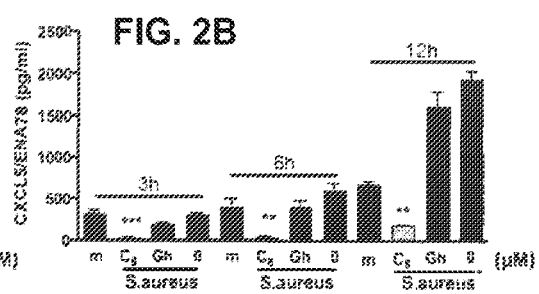
Figure 2C:
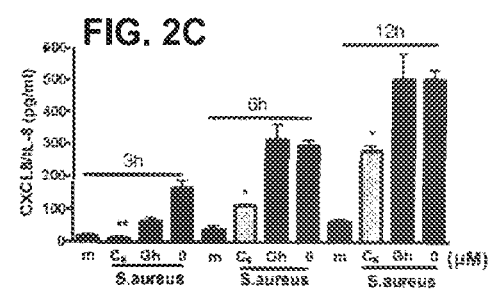
Figure 2D:
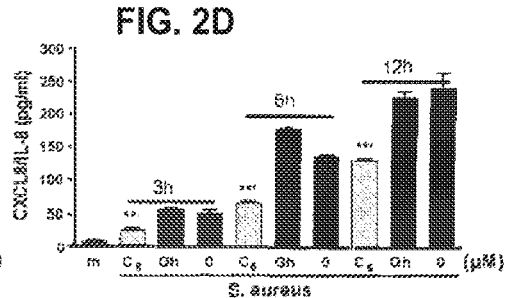

To determine the effect of Lip-C6 on TLR-induced CXC chemokine production, human corneal epithelial (HCE) cells were briefly exposed (30 min) to Lip-C6 or control/ghost (non-C6) liposomes, washed, and incubated with inactivated S. aureus, which activates TLR2 in addition to a specific synthetic TLR2 ligand, Pam3Cys. As a further control, we used Lip-sphingosine-1-P (S1P), a ceramide metabolite linked to mitogenesis. As shown in FIG. 1A, CXCL1, CXCL5 and CXCL8 was produced in response to stimulation with S. aureus. Control (ghost) liposomes had no effect on constitutive or stimulated chemokine production; however, exposure to Lip-C6 completely inhibited S. aureus-induced and Pam3Cys-induced CXCL1, CXCL5 and CXCL8 production. In contrast, S1P did not reduce chemokine production, and in the case of CXCL8/IL-8, S1P actually augmented chemokine production by S. aureus. To ascertain the effect of Lip-C6 on TLR2-stimulated primary epithelial cells, human corneal epithelial cells were isolated from donor corneas and incubated with Pam3Cys in the presence of Lip-C6 or ghost liposomes. As shown in FIG. 1B, Lip-C6, but not control, ghost liposomes inhibited production of CXCL1, CXCL5 and CXCL8 by primary human corneal epithelial cells.

To determine the inhibitory effect of Lip-C6 over a 12 hr period of TLR2 stimulation, HCE cells were pre-incubated with Lip-C6 or control, ghost liposomes prior to addition of S. aureus. Cell supernatants were collected at 3 hrs, 6 hrs and 12 hrs, and chemokine production was measured by ELISA. As shown in FIG. 2, cytokine production by Lip-C6 treated cells was significantly lower than control cells as early as 3 hrs, and continued until 12 hrs after S. aureus stimulation. Taken together, these data clearly demonstrate that Lip-C6 inhibits TLR2-induced CXC chemokine production by human corneal epithelial cells in a dose and time-dependent manner.

Example 13

Localization of Lip-C6

Figure 3:
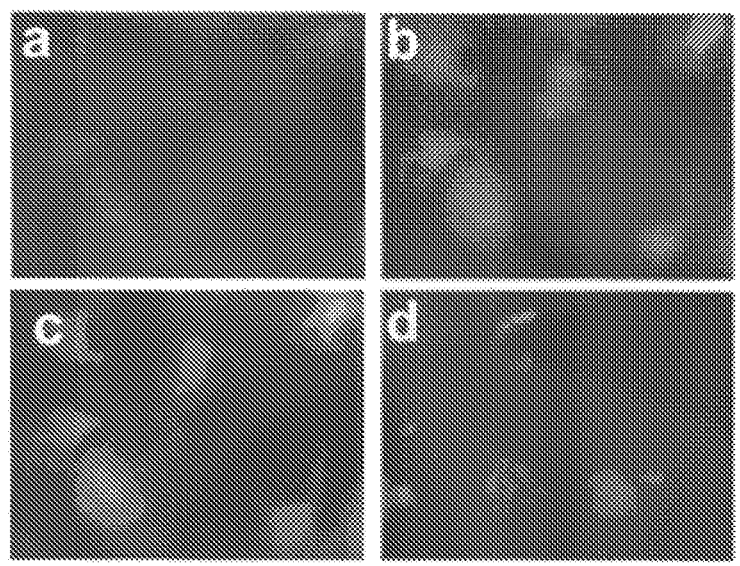
FIG. 3 is a series of micrographs showing intracellular localization of Lip-C6. Human corneal epithelial cells were incubated with NBD labeled Lip-C6 (a), and were counterstained with either Bodipy™-labeled ceramide as a Golgi marker (b, c) or Mito-Tracker red (d). Lip-C6 co-localized with Golgi (panel c). Final magnification using an ×63 objective with 1.6 further magnification is ×1008.

To identify the cellular localization of Lip-C6, liposomes were prepared using C6-NBD, and were incubated with HCE cells and counter-stained with either Bodipy™-labeled ceramide as a Golgi marker (InVitrogen) or with Mito-Tracker red. As shown in FIG. 3, Lip-C6-NBD co-localized with ceramide (a-c), but not with mitochondria (d), demonstrating that the lipid formulation of C6 localizes to the same site as soluble ceramide.

Example 14

Apoptosis Detection

Figure 4A:
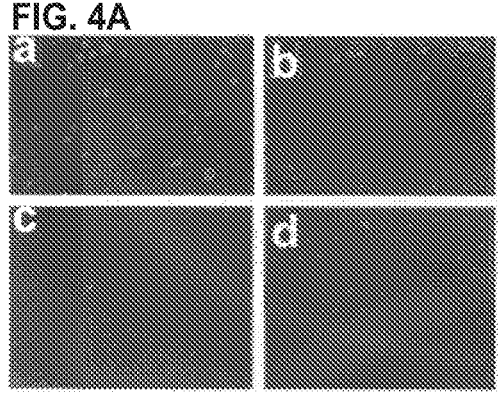
FIGS. 4A and 4B show the effect of Lip-C6 on HCE cell apoptosis.
Figure 4B:
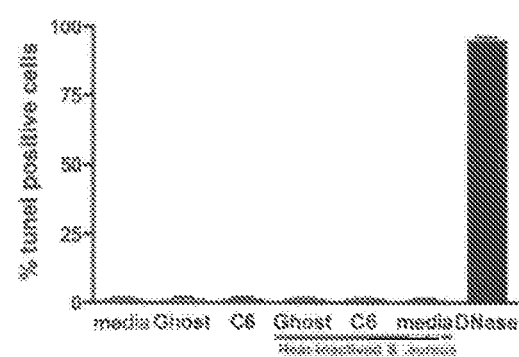

To determine if Lip-C6-mediated inhibition of CXC chemokines was due to induction of a pro-apoptotic response, HCE cells were incubated with S. aureus and either Lip-C6 or ghost liposomes for 18 hrs, and apoptosis was measured by TUNEL assay. As shown in FIG. 4A,B, fewer than 2% TUNEL positive cells were detected in any of the groups, including Lip-C6-treated cells, whereas 100% cells were TUNEL positive after DNAse treatment. This finding indicates that Lip-C6 inhibits CXC chemokine production without inducing apoptosis.

Example 15

Inhibition of p38 and JNK Phosphorylation

To examine the effect of Lip-C6 on p38 and JNK, HCE cells were incubated with 5 µM Lip-C6 or ghost liposomes for 30 min., and S. aureus was added for an additional 6 hrs. HCE cells were then processed for SDS-PAGE and Western Blot analysis using Ab to total and phosphorylated JNK and p38.

Figure 5:
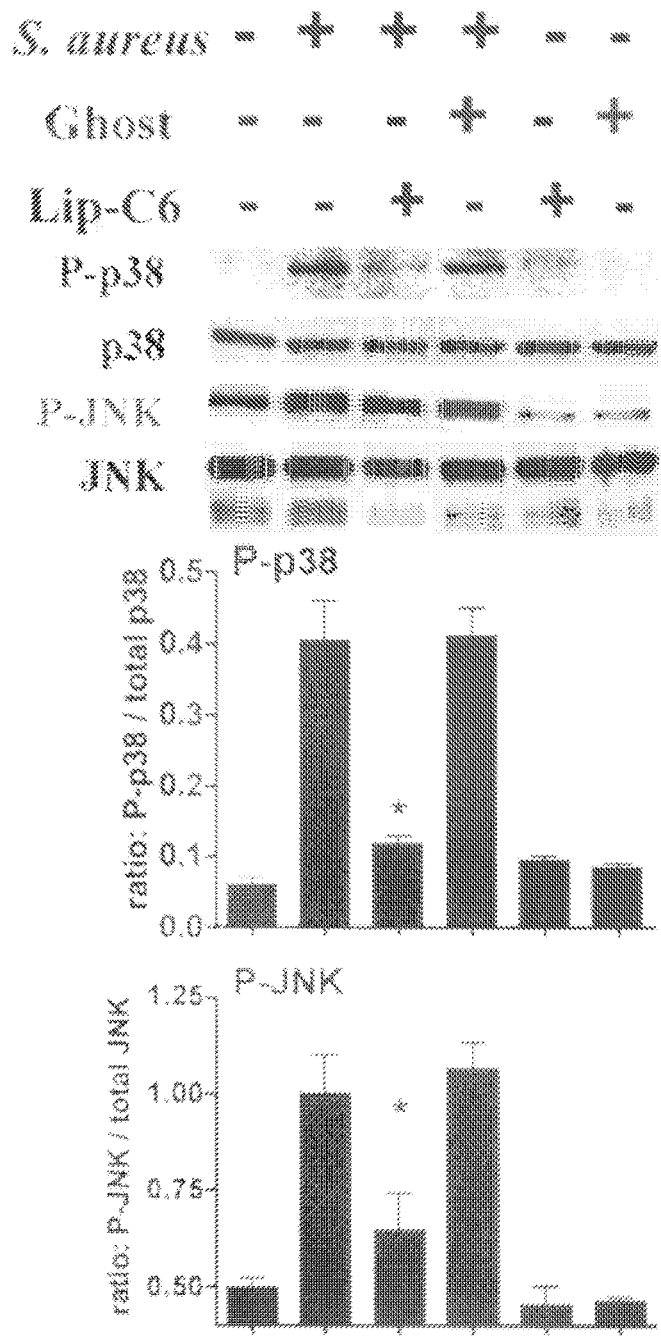
FIG. 5 shows the effect of Lip-C6 on p38 and JNK phosphorylation. Human corneal epithelial cells were incubated with Lip-C6 or ghost liposomes for 30 min prior to addition of S. aureus. After 6 hrs, cells were processed for SDS-PAGE and Western blot analysis using Abs to phosphorylated and non-phosphorylated forms of p38 and JNK. Bands were scanned by densitometry, and the ratio of phosphorylated to non-phosphorylated forms were quantified, and the mean+/−SEM of three independent experiments is shown. Inhibition of P-p38 and P-JNK occurred after incubation with Lip-C6.

As shown in FIG. 5, JNK and p38 were phosphorylated after stimulation with S. aureus. Furthermore, phosphorylation was blocked by Lip-C6 but not by control (ghost) liposomes. As p38 and JNK are involved in inflammatory processes, including CXC chemokine production, these findings indicate that the anti-inflammatory effect of C6 is, in part, due to inhibition of p38 and JNK phosphorylation.

Example 16

Neutrophil Recruitment Inhibition

The effect of Lip-C6 in vivo was examined to determine if Lip-C6 inhibits LPS- or S. aureus-induced corneal inflammation. 2 nMole (811 ng) of either Lip-C6 or control liposomes in 2 µl was either: i) injected into the subconjunctival space; ii) applied topically after inducing a 1 mm diameter corneal abrasion; or iii) applied using both modalities. After 30 min, abraded corneas were treated with either the TLR2 agonist S. aureus or the TLR4 agonist LPS. Mice were sacrificed 18 hrs later, and neutrophil recruitment to the corneal stroma was determined by immmunohistochemistry using NIMP-R14, and the number of neutrophils per 5 µm section was examined by direct counting.

Figure 6A:
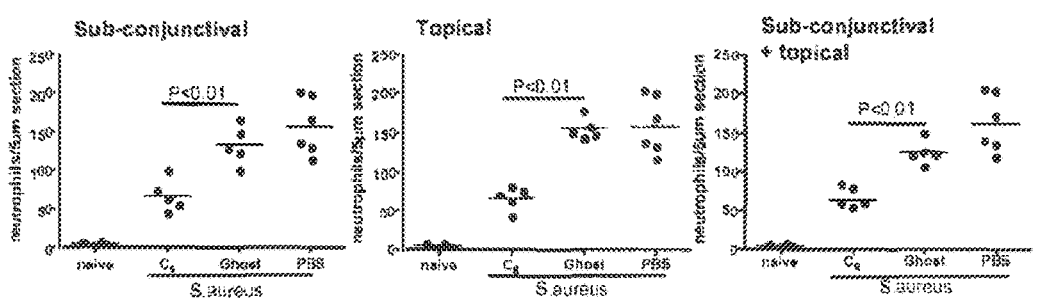
FIGS. 6A and 6B show the effect of sub-conjunctival and topical application of Lip-C6 on neutrophil recruitment to the corneal stroma in mouse models of S. aureus-(FIG. 6A) and LPS- (FIG. 6B) induced corneal inflammation. Lip-C6 or ghost liposomes were either injected into the subconjunctival space, topically applied to a 1 mm diameter region in the central cornea, or were applied by both methods. After 40 min, corneas were stimulated with either inactivated S. aureus (FIG. 6A) or LPS (FIG. 6B), and all were given a second topical application of ghost or Lip-C6 after 6 hrs. After 24 hrs, eyes were snap frozen and neutrophil numbers in a 5 µm corneal section were determined after immunostaining. Data points represent individual corneas from each group of mice. Corneas given Lip-C6 by each of these protocols had significantly less neutrophils than control ghost liposomes. The experiment was repeated three times with similar results.
Figure 6B:
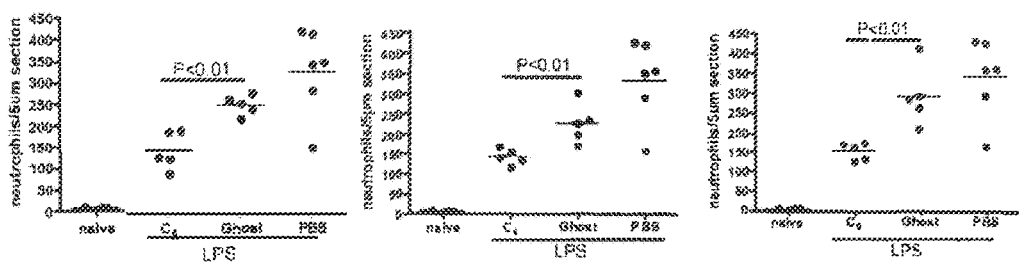

As shown in FIG. 6, *S. aureus* or LPS applied to the abraded corneal surface induced a pronounced neutrophil infiltration to the corneal stroma within 24 hrs. However, we found that Lip-C6 administered by sub-conjunctival injection, topical application, or both treatments significantly inhibited neutrophil recruitment to the corneal stroma. Furthermore, we found that there was no difference in inhibitory activity between these modalities.

Example 17

Effect of Topical Lip-C6 on Corneal Thickness and Haze

Figure 7:
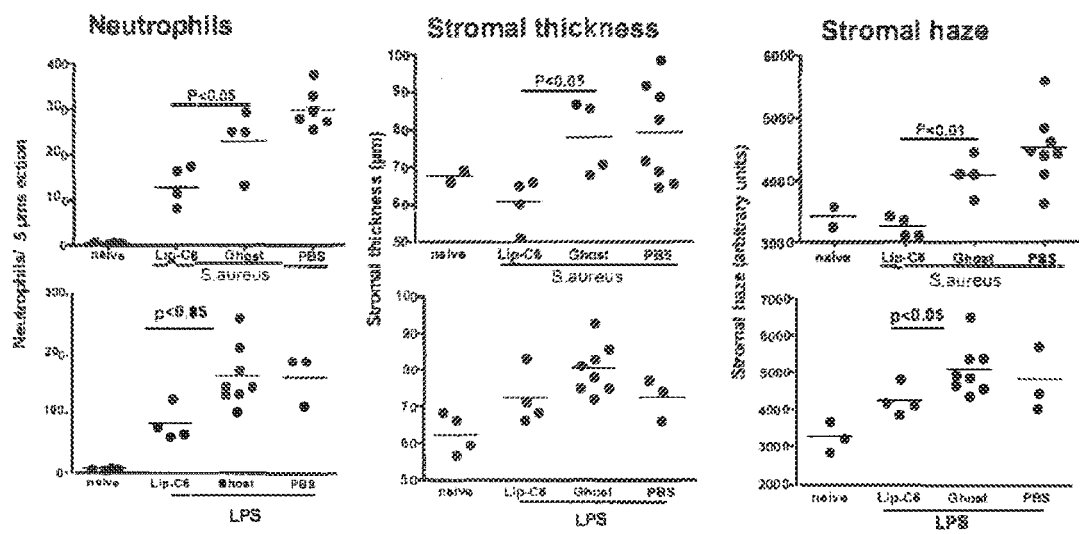
FIG. 7 shows the effect of topical Lip-C6 on S. aureus- and LPS-induced increased corneal thickness and haze. A 1 mm diameter wound was made in the central corneal stroma of C57BL/6 mice, and topical Lip-C6 was given 1 hr before and 6 hrs after exposure to S. aureus. After 24 hrs, neutrophils were detected by immunohistochemistry, corneas were by in vivo confocal microscopy, and corneal thickness and haze were calculated as described in herein.

To assess the effect of topical Lip-C6 on TLR2-induced corneal thickness and haze, corneas were abraded as before, control or Lip-C6 was added one hour before and 6 hrs after stimulation with $1\times10^7$ UV inactivated *S. aureus* or 40 µg LPS. After 24 hrs, corneas were examined by in vivo confocal microscopy (Confoscan™), and increases in corneal thickness and haze were measured using Navis™ software as described in Refs. 1 and 8. Neutrophils were detected by immunohistochemistry as before. FIG. 7 shows that Lip-C6 administered topically not only inhibited neutrophil recruitment to the corneal stroma, but also prevented development of increased corneal thickness and haze induced by *S. aureus* or LPS.

Example 18

Lip-C6 does not Prevent Corneal Epithelial Wound Healing

As corneal wound healing requires epithelial cell proliferation and migration, the effect of Lip-C6 in this process was examined. A one mm diameter wound was made in the corneal epithelial layer as described above, and corneas were pre-treated for 30 min with Lip-C6 or ghost liposomes, and exposed to *S. aureus*. Fluorescein was added to the corneal surface at 0 hr, 6 hrs and 24 hrs after abrasion. As fluorescein binds only to sites where the corneal epithelium is not intact or contiguous, the area of fluorescein binding shows the area of the wound, and conversely fluorescein exclusion indicates wound healing. As shown in FIG. 8A, fluorescein was present on the wound at 0 hr and 6 hrs in control (ghost) and Lip-C6 treated corneas exposed to *S. aureus*. Fluorescein was undetectable after 24 hrs, indicating complete wound healing. The rate of corneal wound healing was not inhibited by Lip-C6 or control liposomes in the presence of *S. aureus* (FIG. 8B). Similarly, H&E stained sections of representative corneas treated with Lip-C6 show that the corneal epithelium is absent at 6 hrs, and has regenerated after 24 hrs (FIG. 8C). Similar results were observed in all control groups (data not shown), thereby demonstrating that the anti-inflammatory activity of C6-ceramide is not due to impaired corneal wound healing.

To determine if Lip-C6 induces corneal epithelial cell apoptosis, corneal sections were stained for TUNEL reactivity and counterstained with DAPI. FIG. 8D shows that TUNEL positive cells were not detected in the stroma or epithelium of either naïve corneas (a) or corneas treated with Lip-C6 and *S. aureus* (b). TUNEL positive corneal epithelial cells were not detected in any of the experimental groups (not shown), thereby demonstrating that Lip-C6 has no pro-apoptotic effect on epithelial cells in vivo.

These observations support the conclusion that Lip-C6 suppresses corneal inflammation by inhibiting CXC chemokine production and resultant neutrophil recruitment to the corneal stroma rather than promoting epithelial cell apoptosis.

Example 19

Lip-C6 Inhibits TLR2- and TLR4-Induced Neutrophil Activation

Figure 9A:
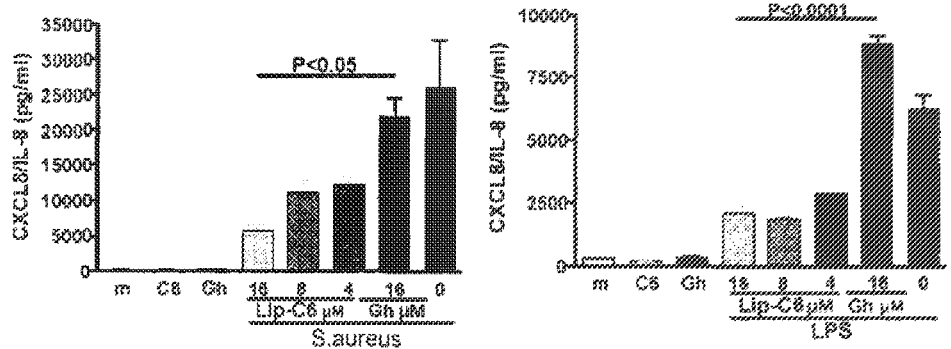
FIGS. 9A, 9B and 9C show the effect of Lip-C6 on TLR2 and TLR4-induced inflammation on human and murine neutrophils.

We examined the effect of Lip-C6 on TLR-induced neutrophil CXC chemokine production. A human neutrophil cell line (HL-60) was stimulated in vitro with *S. aureus* or LPS, and CXCL8/IL-8 production was measured by ELISA. As shown in FIG. 9A, CXCL8/IL-8 is produced by the human neutrophil cell line in response to *S. aureus* or LPS stimulation; however, pre-incubation with Lip-C6 significantly inhibits CXC production compared with ghost liposome.

Figure 9B:
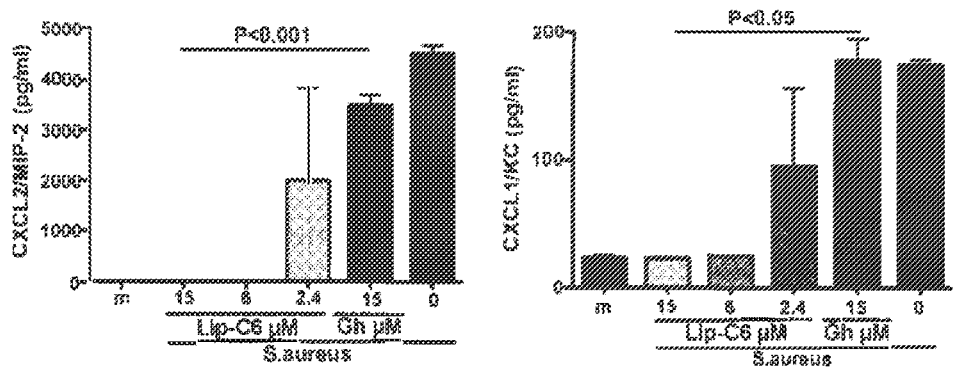
Figure 9C:
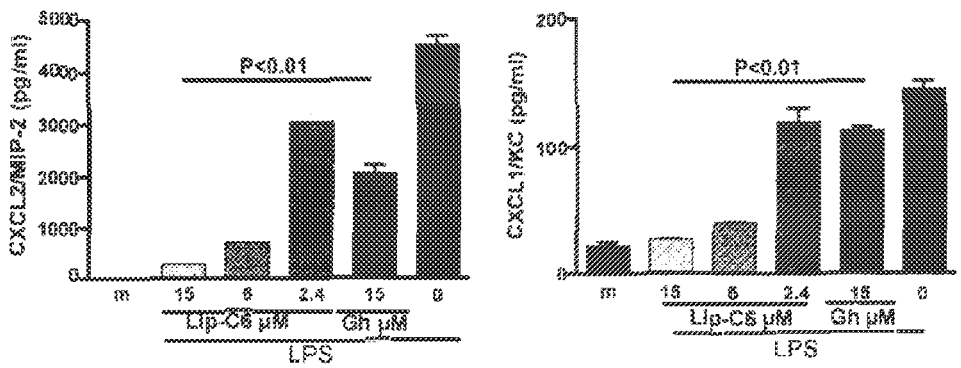

As CXC chemokine production by neutrophils likely mediates further neutrophil infiltration to the corneal stroma and subsequent development of keratitis, we also examined the effect of Lip-C6 on an enriched (>98%) population of mouse peritoneal neutrophils. As shown in FIGS. 9B and C, pre-incubation of murine neutrophils with ghost liposomes or Lip-C6 confirmed the results with human neutrophils (FIG. 9A), with Lip-C6 inhibiting TLR2- and TLR4-induced CXCL1 and CXCL2 production in a dose dependent manner.

Statistical analysis was performed using an unpaired t-test (Prism; Graph Pad Software, San Diego, Calif.). A p value of less than 0.05 was considered significant.

INCORPORATION BY REFERENCE

All publications mentioned in this specification are incorporated herein by reference to the same extent as if each individual publication is specifically and individually indicated to be incorporated by reference.

1. Johnson A C, Heinzel F P, Diaconu E, et al. Activation of toll-like receptor (TLR)2, TLR4, and TLR9 in the mammalian cornea induces MyD88-dependent corneal inflammation. *Invest Ophthalmol Vis Sci* 2005; 46:589-595.
2. Khatri S, Lass J H, Heinzel F P, et al. Regulation of endotoxin-induced keratitis by PECAM-1, MIP-2, and toll-like receptor 4. *Invest Ophthalmol Vis Sci* 2002; 43:2278-2284.
3. Stover T, Kester M. Liposomal delivery enhances short-chain ceramide-induced apoptosis of breast cancer cells. *J Pharmacol Exp Ther* 2003; 307:468-475.
4. Stover T C, Sharma A, Robertson G P, Kester M. Systemic delivery of liposomal short-chain ceramide limits solid tumor growth in murine models of breast adenocarcinoma. *Clin Cancer Res* 2005; 11:3465-3474.
5. Kruszewski F H, Walker T L, DiPasquale L C. Evaluation of a human corneal epithelial cell line as an in vitro model for assessing ocular irritation. *Fundam Appl Toxicol* 1997; 36:130-140.
6. Ueta M, Nochi T, Jang M H, et al. Intracellularly expressed TLR2s and TLR4s contribution to an immunosilent environment at the ocular mucosal epithelium. *J Immunol* 2004; 173:3337-3347.
7. Adhikary G, Crish J, Lass J, Eckert R L. Regulation of involucrin expression in normal human corneal epithelial cells: a role for activator protein one. *Invest Ophthalmol Vis Sci* 2004; 45:1080-1087.
8. Sun Y, Hise A G, Kalsow C M, Pearlman E. *Staphylococcus aureus*-induced corneal inflammation is dependent on Toll-like receptor 2 and myeloid differentiation factor 88. *Infect Immun* 2006; 74:5325-5332.

9. Hauert A B, Martinelli S, Marone C, Niggli V. Differentiated HL-60 cells are a valid model system for the analysis of human neutrophil migration and chemotaxis. *Int J Biochem Cell Biol* 2002; 34:838-854.

While the invention has been explained in relation to embodiments, it is to be understood that various modifications thereof will become apparent to those skilled in the art upon reading the specification. Therefore, it is to be understood that the inventions disclosed herein are intended to cover such modifications as fall within the scope of the appended claims, and to cover insubstantial variations thereof.

The invention claimed is:

1. A method for treating ocular tissue injury or diseases comprising administering to a subject in need thereof a composition comprising a $C_6$-ceramide containing nanoliposome, wherein the ocular disease is a disease associated with neutrophil infiltration in a cell.

2. The method of claim 1 wherein the ceramide thereof is administered at a dosage of about 1 nanogram to about 100 micrograms per day.

3. The method of claim 1 wherein the composition inhibits mitogen-activated protein (MAP) kinases signaling.

4. The method of claim 3 wherein the MAP kinases is at least one of JNK and p38.

5. The method of claim 1 wherein the ceramide down-regulates chemotactic mediators that recruit neutrophils to the site of tissue injury via Toll-like and cytokine receptors.

6. The method of claim 1 wherein the ocular disease is a disease of the anterior eye.

7. The method of claim 6 wherein the ocular disease is at least one of keratitis, endophthalmitis, uveitis, conjunctivitis, blepharitis, contact lens-induced peripheral ulcer and corneal dystrophy.

8. The method of claim 1 wherein the ocular disease is a disease of the posterior eye.

9. The method of claim 8 wherein the ocular disease is at least one of retinitis pigmentosa, diabetic retinopathy, macular degeneration and ocular toxoplasmosis.

10. The method of claim 1 wherein the ocular disease is caused by refractive or laser surgery.

11. A method for preventing ocular diseases associated with neutrophil infiltration in a cell comprising administering to a subject in need thereof a composition comprising a $C_6$-ceramide containing nanoliposome.

12. The method of claim 11 wherein the ocular disease is a disease of the anterior eye.

13. The method of claim 12 wherein the ocular disease is at least one of keratitis, endophthalmitis, uveitis, conjunctivitis, blepharitis, contact lens-induced peripheral ulcer and corneal dystrophy.

14. The method of claim 11 wherein the ocular disease is a disease of the posterior eye.

15. The method of claim 14 wherein the ocular disease is at least one of retinitis pigmentosa, diabetic retinopathy, macular degeneration and ocular toxoplasmosis.

* * * * *